United States Patent [19]

Cross

[11] Patent Number: 5,006,791
[45] Date of Patent: Apr. 9, 1991

[54] ELECTROSTATIC DETECTOR AND METHOD FOR DETECTING CONDUCTORS

[75] Inventor: Dan A. Cross, Seattle, Wash.

[73] Assignee: The Boeing Company, Seattle, Wash.

[21] Appl. No.: 798,996

[22] Filed: Nov. 18, 1985

[51] Int. Cl.$^5$ .................. G01R 19/14; G01R 31/08
[52] U.S. Cl. .................... 324/133; 324/515
[58] Field of Search .............. 324/61 R, 61 P, 133, 324/515, 516, 517, 518, 558, 554, 559; 200/DIG. 1; 340/870.31, 365 E; 361/280

[56] References Cited

U.S. PATENT DOCUMENTS

| | | | |
|---|---|---|---|
| 2,823,425 | 2/1959 | Huggins | 324/517 |
| 3,413,541 | 11/1968 | Swim et al. | 324/515 |
| 4,016,490 | 4/1977 | Weckenmann et al. | 324/61 P |
| 4,334,188 | 6/1982 | Dudley | 324/133 |

Primary Examiner—W. Snow
Attorney, Agent, or Firm—Christensen, O'Connor, Johnson & Kindness

[57] ABSTRACT

A circuit is disclosed for detecting a conductive region in a body. The circuit includes a remote module (12) coupled to a driver and logic module (14). The remote module is mountable on a probe (16) and senses contact between a conductive detector electrode and the conductive region. The driver and logic module provides energy to the remote module and responds to the operation of the remote module by producing an output indicative of detection of the conductive region. In the preferred arrangement, current from a constant current source $Q_4$ normally flows through a first transistor $Q_1$, which is maintained in an "on" state by a charged capacitor $C_1$. When the detector electrode contacts the conductive region, however, charge is bled from the capacitor, switching the first transistor to an "off" state and causing the current from the current source to be redirected to a switching transistor $Q_3$. As a result, the switching transistor momentarily switches to an "on" state, causing a latch (18) to set a status signal at terminal S indicating detection of the conductive region.

18 Claims, 1 Drawing Sheet

ELECTROSTATIC DETECTOR AND METHOD FOR DETECTING CONDUCTORS

The U.S. Government has rights to this invention pursuant to Contract No. DAAH01-82-D-0013-0003 awarded by the U.S. Army.

SUMMARY OF THE INVENTION

This invention is directed to a detector and method for detecting a conductive region in a body. The detector includes a conductive detector electrode for contacting the conductive region. An electrical charge is established on the electrode, and circuit elements detect a decrease in the potential when the electrode contacts the conductive region.

DETAILED DESCRIPTION OF THE PREFERRED EMBODIMENT

Figure 1:
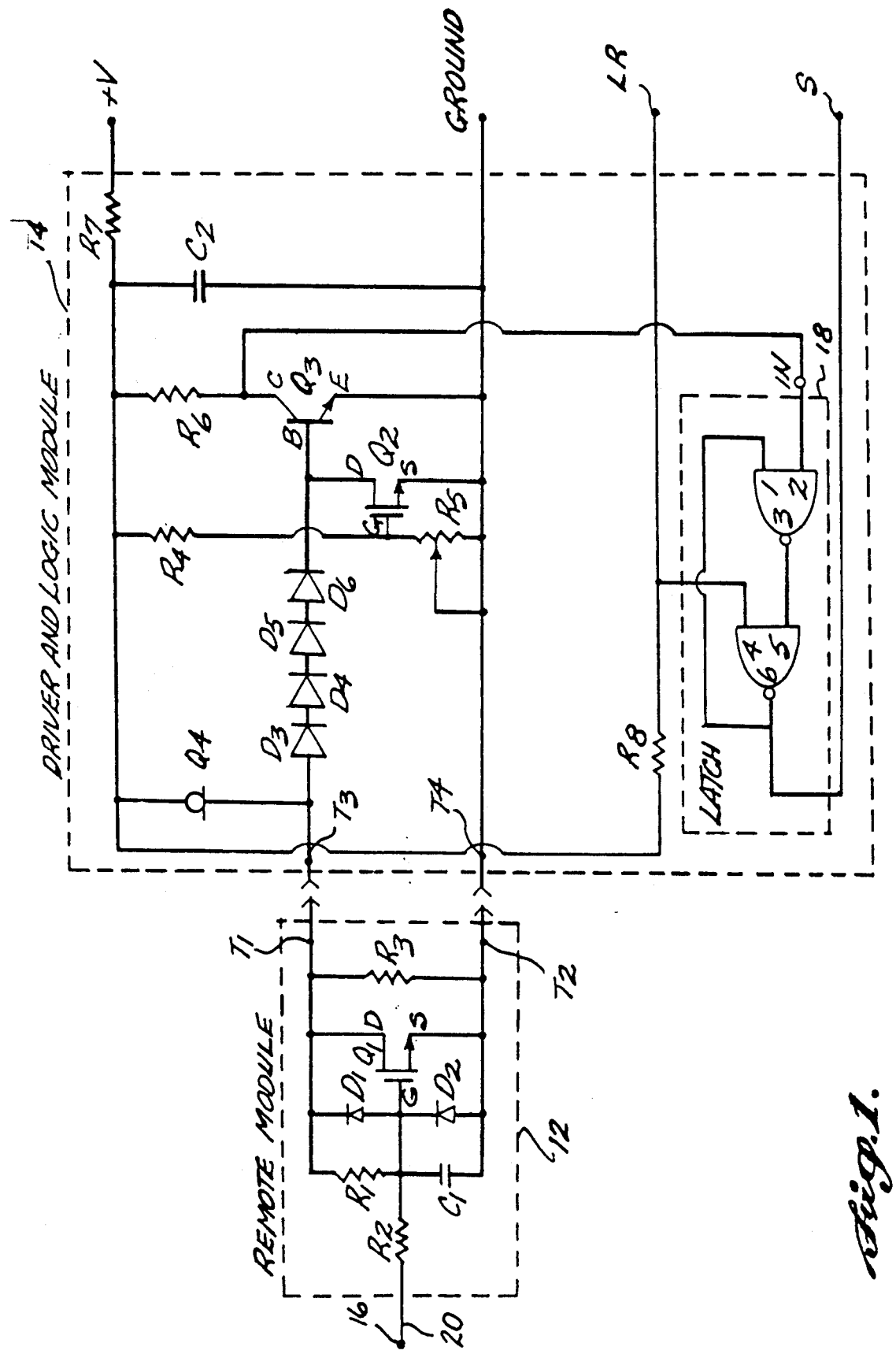
FIG. 1 is a schematic diagram of the detector circuit.

The detector circuit of the present invention generally includes a remote module 12 mounted on a probe 16 and a driver and logic module 14. A cable provides electrical connection between terminals T1 and T2 of the remote module 12 and terminals T3 and T4, respectively, of the driver and logic module 14. The driver and logic module is connected to a power supply (not shown) through the terminals designated "+V" and "ground". The driver and logic module also is connected to a microprocessor (not shown) through a latch reset terminal and a status terminal.

In its ready mode, a steady state condition exists in which current flows from a constant current source Q4 (such as a 1N5290 diode) through an insulated gate field-effect transistor Q1 that is maintained in the on state when a capacitor C1 is fully charged. The capacitor and transistor are connected with the probe via a bleed resistor R2 and a lead 20. The electrical potential of the detector sleeve (induced by charge stored by capacitor C3) remains relatively constant as long as the probe contacts nonconducting material. When contact is made between the probe and a conductive material, such as a terminal of the trailing end of the wire segment sliding through the probe, the electrical potential of the probe decreases causing the charge stored by capacitor C1 to decrease as current flows from capacitor C1 to the probe and into the conductive material. As a result, the potential at the transistor gate decreases to a level sufficient to momentarily turn off the field-effect transistor, while the capacitor C1 recharges through resistor R1. When field-effect transistor Q1 is off, the potential at the junction of current source Q4 and resistor R1 is sufficient to cause forward current through a series of diodes (D3, D4, D5, and D6) and turn on a switching transistor Q3. This causes the collector of transistor Q3 to switch momentarily from its high condition (approximately +V) to its low condition (slightly above ground potential) to set a status signal at terminal S.

The bleed resistor R2 slows the bleed of charge from the capacitor C1 to control the time constant of the transient pulse. The component values of resistor R1 and capacitor C1 determine the stability and sensitivity of the system. Diodes, D1 and D2, and resistor R3 protect transistor Q1 from potentially harmful transients.

In the driver and logic module 14, the diodes D3, D4, D5, and D6 provide a potential at the junction between the current supply Q4 and diode D3 that is sufficient to operate the remote module 12 or forward leakage. A second insulated gate field-effect transistor Q2 is connected between the base electrode of transistor Q3 and ground. A voltage divider network consisting of resistor R4 and variable resistor R5 biases the gate electrode of transistor Q2 so that reverse or forward leakage current flow through diodes D3–D6 is shunted to ground through the transistor Q2.

The latch 18 is of conventional design and is connected in such a way that, when a low appears on pin 2 as a result of transistor Q3 switching low, the latch output on pin 6 also goes low, (and is latched low) supplying a status signal that indicates detection of the trailing end of the wire segment. A momentary low on the latch reset input (pin 4) via the latch reset terminal LR returns the latch to the ready mode.

Resistor R6 is the load resistor for transistor Q3, and resistor R8 maintains latch reset terminal 4 at approximately +V, in the absence of a reset signal. Capacitor C2 ensures that the pulse is passed through the circuit and is detected. Resistor R7 and capacitor C2 also provide noise filtering.

In operating, the microprocessor (not shown) supplies a signal to the latch reset terminal LR to place the probe in the ready state. When the probe contacts a conductor, the detector circuit supplies the microprocessor with the detection status signal.

The circuit of the present invention is particularly suited for applications where only one contact can be made between the probe 16 and the conductor. The electrostatic technique used detects the charge drain caused by the contact and creates a status signal. A simple, yet highly sensitive detector can be easily produced with accuracy tailored to the need. Sensitivity is improved by separating the remote module and the driver and logic module, since this feature reduces the area of the conductive portion of the probe 16 between the capacitors and probe tip.

While a preferred embodiment has been shown and described, those skilled in the art will recognize alterations, modifications, and variations that might be made to these embodiments without departing from the inventive concept. Therefore, the claims should be interpreted liberally to protect the described embodiments and their reasonable equivalents. The description and drawings are meant to illustrate the invention and are meant to limit the invention only insofar as limitations are necessary in view of the pertinent prior art.

The embodiments of the invention in which an exclusive property or privilege is claimed are defined as follows:

1. A detector for detecting a conductive region, comprising:
   a conductive detection electrode for contacting the conductive region;
   a capacitor for establishing an electrical charge on said detection electrode to place said detection electrode at a predetermined electrical potential;
   means for detecting a decrease in said electrical potential of said detection electrode when said conductive region contacts said detection electrode;
   first and second circuit terminals connectable to a source of operating potential;
   a current source for supplying a control current in response to said operating potential, the first end of said current source being connected to said first circuit terminal and the second end of said current source being connected to the first terminal of said capacitor, the second terminal of said capacitor being connected to said second circuit terminal, the first terminal of said capacitor also being connected to said detection electrode; and a first transistor switch having a control electrode connected to the first terminal of said capacitor, said first transistor switch for directing said control current to said second circuit terminal when said potential of said detection electrode remains at a predetermined potential and for blocking said control current when said potential on said detection electrode decreases from said predetermined level.

2. The detector of claim 1, further comprising a second transistor switch and means coupled to said current source for receiving said control current and for supplying said control current to the control electrode of said second transistor switch only when said control current is blocked by said first transistor switch, said second transistor switch being in a first nonconductive state when said control current is not blocked by said first transistor switch and being switched to a second conductive state when said control current is blocked by said first transistor switch; said second transistor switch supplying a switch signal indicating that said transistor switch is in said second conductive state.

3. The detector of claim 2, further comprising a latch circuit having an output terminal, an input terminal and a reset terminal; said latch circuit being responsive to a logic signal applied to said reset terminal for establishing a first output potential at said output terminal, said input terminal being coupled to said second transistor switch for receiving said switch signal, said latch circuit being responsive to said switch signal to establish a second output at said output terminal.

4. A detector for detecting a conductive terminal installed on the end of an insulated wire, comprising:
a conductive detector electrode for contacting said terminal; and
an electronic circuit having:
  (a) an input terminal for connection to said detector electrode;
  (b) a capacitor connected to said input terminal for establishing an electrical charge on said detector electrode that places said detector electrode at a predetermined potential;
  (c) means connected to said capacitor and responsive to the electrical potential of said capacitor for supplying a signal when said electrical potential decreases below a predetermined level;
  (d) first and second circuit terminals for receiving an operating potential;
  (e) a first resistor connected between the first terminal of said capacitor and said detector electrode, the second terminal of said capacitor being connected to said second circuit terminal;
  (f) a circuit branch including a current source and a second resistor connected in series with said current source, said current source being connected to said first circuit terminal and responsive to said operating potential, said second resistor being connected to said first terminal of said capacitor; and
  (g) a first field-effect transistor having the gate electrode thereof connected to said first terminal of said capacitor, the drain electrode connected to the junction between said current source and said second resistor and the source electrode connected to said second circuit terminal.

5. The detector of claim 4, wherein said electronic circuit further includes a bipolar transistor and a third resistor; said bipolar transistor having its base electrode connected to said drain electrode of said first field effect transistor, its emitter electrode connected to said second circuit terminal and its collector electrode connected to said first circuit terminal by means of said third resistor.

6. The detector of claim 5, wherein said electronic circuit further comprises a latch circuit having an input terminal, a reset terminal and an output terminal, said latch circuit being responsive to a logic signal applied to said reset terminal for establishing the electrical potential at said output terminal of said latch circuit at a first predetermined output potential, said input terminal of said latch circuit being connected to said collector electrode of said bipolar transistor; said latch circuit being responsive to a signal at said collector electrode of said bipolar transistor to establish the electrical potential at said output terminal of said latch circuit at a second predetermined output potential.

7. The detector of claim 6, wherein said electronic circuit includes at least one diode connected between said drain electrode of said first field effect transistor and said base electrode of said bipolar transistor.

8. The detector of claim 7, wherein said electronic circuit further includes a second field effect transistor having its drain electrode connected to said base electrode of said bipolar transistor and its source electrode connected to said first operating potential; said electronic circuit further including bias means for establishing the drain-to-source current of said second field effect transistors at a value that allows said bipolar transistor to change operating states only when said potential at said capacitor is below said predetermined value.

9. A method for detecting a conductive region, comprising the steps of:
inducing an electrical potential on a conductive detector electrode; and,
monitoring the electrical potential of said detector electrode to detect a decrease in said electrical potential upon contact between the electrode and the conductive region,
wherein the step of inducing said electrical potential includes the step of charging a capacitor having one terminal connected to said detector electrode and said step of monitoring includes the step of detecting a decrease in the electrical potential across said capacitor, and
wherein the step of charging said capacitor includes the step of supplying a current signal to said capacitor and said step of detecting a decrease in said electrical potential across said capacitor includes the steps of blocking the flow of a control current through a field-effect transistor connected to said capacitor and directing the control current to a switch circuit to activate the switch circuit when said potential across said capacitor decreases.

10. A detector for detecting a conductive region in a material, comprising:
a conductive detection electrode for providing a single point of contact between the detector and the otherwise unconnected region;
an insulated gate field-effect transistor controllably operable between an on state and an off state;
a capacitor connected to the electrode and to the transistor so that the state of the transistor is controlled by the amount of static charge stored by the capacitor independent of active current flow from the capacitor;

means for charging the capacitor; and means, responsive to a transient decrease in charge on the capacitor through a bleed of charge to the detected region from the capacitor when the electrode contacts the region and thereby through a momentary switching off of the field-effect transistor, for setting a latch to indicate detection of the region.

11. A detector for detecting a conductive region in a material comprising:

a conductive detection electrode for contacting the region;

an insulated gate field-effect transistor;

a capacitor connected to the electrode and to the transistor so that the transistor is on when the capacitor is fully charged;

means for charging the capacitor;

a bleed resistor connected between the electrode and the capacitor to control the time constant for the bleed of charge from the capacitor; and means, responsive to a transient decrease in charge on the capacitor through a bleed of charge to the detected region from the capacitor when the electrode contacts the region and thereby through a momentary switching off of the field-effect transistor, for setting a latch to indicate detection of the region; wherein the means for setting the latch includes:

(a) at least one diode;

(b) a switching transistor having a base terminal and a collector terminal, the base terminal being connected to the field-effect transistor through said diode and the collector terminal being connectable to the latch; and (c) bias means connected to the base terminal of the switching transistor for ensuring that a momentary current pulse through the diode will be directed through the base terminal to switch the switching transistor.

12. The detector of claim 11 further comprising a bleed resistor connected between the electrode and the capacitor to control the time constant for the bleed of charge from the capacitor.

13. The detector of claim 11 wherein the bias means includes a second field-effect transistor and a voltage divider network including a fixed resistor connected between the means for charging the capacitor and the gate of the second field-effect transistor and a variable resistor connected between the gate of the second field-effect transistor and ground.

14. The detector of claim 10 wherein the means for charging the capacitor includes a constant current source.

15. The detector of claim 13 wherein the means for charging the capacitor includes a constant current source.

16. A detector for detecting a conductive region in a material, comprising:

a detection electrode;

a capacitor connected to the electrode;

a field-effect transistor having its gate connected to the electrode and charge plate of the capacitor so that the capacitor holds the gate on when the capacitor is fully charged;

a substantially constant current source connected to the capacitor for charging the capacitor;

a switching transistor, coupled to the current source and the field-effect transistor, for receiving current from the current source when the field-effect transistor switches off in response to a decrease in charge on the capacitor caused by contact of the electrode with the region; and a latch connected to the switching transistor and set when the switching transistor responds to current.

17. A method for detecting a conductive region in a material, comprising the steps of:

charging a capacitor to a predetermined potential sufficient to hold a first transistor connected to the capacitor in the "on" state;

contacting the capacitor with the region to cause a decrease in the potential by a bleed of charge from the capacitor to the region;

sensing the decrease by switching off the first transistor; and throwing a latch in response to switching off the transistor, said step of throwing the latch including:

redirecting current from the first transistor to the gate of a switching transistor causing the switching transistor to switch from high to low when the first transistor switches off; and setting a status signal in the latch in response to the low of the switching transistor.

18. A method of detecting a conductive region in a material, comprising the steps of:

charging a capacitor to a potential that is sufficient to hold a first transistor connected to the capacitor in an on state;

placing a conductive detection electrode, coupled to the capacitor, in contact with a single point of the material, which is otherwise electrically unconnected to the capacitor and transistor, the presence of a conductive region in the material causing a bleed of charge from the capacitor to the region and a decrease in the capacitor's potential; and switching off the first transistor in response to a decrease in the capacitor's potential to indicate detection of a conductive region.

* * * * *

UNITED STATES PATENT AND TRADEMARK OFFICE
CERTIFICATE OF CORRECTION

PATENT NO. : 5,006,791

DATED : April 9, 1991

INVENTOR(S) : D. A. Cross

It is certified that error appears in the above-identified patent and that said Letters Patent is hereby corrected as shown below:

| COLUMN | LINE | |
|---|---|---|
| 1 | 42 | "C3" should be --C1-- |

Signed and Sealed this

Second Day of March, 1993

Attest:

STEPHEN G. KUNIN

Attesting Officer

Acting Commissioner of Patents and Trademarks